United States Patent
Bäurer

(10) Patent No.: US 10,952,932 B2
(45) Date of Patent: Mar. 23, 2021

(54) BLANK AND METHOD FOR PRODUCING A TOOTH REPLACEMENT PART

(71) Applicant: SIRONA DENTAL SYSTEMS GMBH, Bensheim (DE)

(72) Inventor: Michael Bäurer, Bretten (DE)

(73) Assignee: DENTSPLY SIRONA Inc., York, PA (US)

(*) Notice: Subject to any disclaimer, the term of this patent is extended or adjusted under 35 U.S.C. 154(b) by 0 days.

(21) Appl. No.: 16/322,135

(22) PCT Filed: Aug. 9, 2017

(86) PCT No.: PCT/EP2017/070172
§ 371 (c)(1),
(2) Date: Jul. 9, 2019

(87) PCT Pub. No.: WO2018/029244
PCT Pub. Date: Feb. 15, 2018

(65) Prior Publication Data
US 2019/0328622 A1 Oct. 31, 2019

(30) Foreign Application Priority Data
Aug. 9, 2016 (DE) .......................... 102016214725.0

(51) Int. Cl.
*C04B 35/486* (2006.01)
*A61K 6/818* (2020.01)
(Continued)

(52) U.S. Cl.
CPC .......... *A61K 6/818* (2020.01); *A61C 13/0022* (2013.01); *A61C 13/083* (2013.01); *C04B 35/486* (2013.01); *C04B 35/645* (2013.01); *C04B 2235/3225* (2013.01); *C04B 2235/3244* (2013.01); *C04B 2235/5409* (2013.01)

(58) Field of Classification Search
CPC .... A61K 6/818; C04B 35/645; C04B 35/486; C04B 2235/5409; C04B 2235/3244; C04B 2235/3225; C04B 2235/9661; C04B 2235/77; C04B 2235/661; C04B 2235/6565; C04B 2235/6562;
(Continued)

(56) References Cited

U.S. PATENT DOCUMENTS 5,565,152 A * 10/1996 Od en ................ A61C 13/0003
264/19
6,087,285 A 7/2000 Oomichi
(Continued)

FOREIGN PATENT DOCUMENTS

DE 102016202902 A1 8/2017

OTHER PUBLICATIONS

International Preliminary Report on Patentability Chapter II (IPRP); PCT/EP2017/070172; Oct. 25, 2018 (Completed).
(Continued)

*Primary Examiner* — Noah S Wiese
(74) *Attorney, Agent, or Firm* — Dentsply Sirona Inc.

(57) ABSTRACT

The invention relates to a blank for producing a tooth replacement part using a CAD/CAM device, comprising a block of a sintered material. Said block of sintered material has already been presintered in a sintering furnace at an initial sintering temperature between 1000° C. and 1250° C.

10 Claims, 2 Drawing Sheets

(51) Int. Cl.
*A61C 13/00* (2006.01)
*A61C 13/083* (2006.01)
*C04B 35/645* (2006.01)

(58) Field of Classification Search
CPC ...... C04B 2235/612; C04B 2235/6026; A61C 13/083; A61C 13/0022; A61C 5/77
See application file for complete search history.

(56) References Cited

U.S. PATENT DOCUMENTS

| | | | |
|---|---|---|---|
| 6,133,174 A * | 10/2000 | Brodkin | A61K 6/17 501/6 |
| 6,709,694 B1 * | 3/2004 | Suttor | C04B 35/6263 427/2.26 |
| 8,034,264 B2 | 10/2011 | Ritzberger | |
| 8,231,825 B2 * | 7/2012 | Eriksson | A61C 13/0022 264/16 |
| 8,541,329 B2 | 9/2013 | Ritzberger | |
| 9,186,227 B2 * | 11/2015 | Reinshagen | C04B 35/62818 |
| 9,428,422 B2 | 8/2016 | Kawamura | |
| 9,561,090 B2 | 2/2017 | Eriksson | |
| 10,101,088 B2 | 10/2018 | Schmidt | |
| 2015/0315086 A1 * | 11/2015 | Kawamura | A61K 6/16 501/134 |
| 2016/0195334 A1 | 7/2016 | Rohner | |
| 2016/0317257 A1 | 11/2016 | Fornoff | |

OTHER PUBLICATIONS

Written Opinion of the International searching Authority; PCT/EP2017/070172; Oct. 17, 2017 (completed); dated Oct. 25, 2017.

International Search Report; PCT/EP2017/070172; Oct. 17, 2017 (completed); dated Oct. 25, 2017.

* cited by examiner

BLANK AND METHOD FOR PRODUCING A TOOTH REPLACEMENT PART

TECHNICAL FIELD

The invention relates to a method and a blank for producing a tooth replacement part using a CAD/CAM device comprising a block of a sintered material.

BACKGROUND OF THE INVENTION

A number of blanks for producing tooth replacement parts using a CAD/CAM device are known from the state of the art.

A precolored blank is made of a zirconium dioxide ($ZrO_2$). Iron oxide ($Fe_2O_3$) is frequently used as the dye for yellow coloration. The blanks can also contain aluminum oxide ($Al_2O_3$) as an additive. Prior to processing in the CAM device, the blanks are presintered in a sintering furnace at a temperature up to 1150° C. The blanks typically consist of a powder of ceramic particles held together by means of a polymer. The polymer can have a weight fraction of, for example, 3%. During presintering in the sintering furnace, the polymer is burned out and the ceramic particles are sintered so that the blank is hard enough to be processed by means of the CAM processing machine. The tooth replacement part is then carved out of the presintered blank by means of the CAD/CAM device. The produced tooth replacement part is subsequently sintered to final density in the sintering furnace, as a result of which the required density and hardness of the tooth replacement part is achieved.

One disadvantage of these blanks is that, when sintering larger tooth replacement parts such as bridges to final density, a heating rate in a heating phase may be no more than 50° C./minute. More rapid heating with a higher heating rate would lead to mechanical stresses within the tooth replacement part and possibly result in a fracture. The core of a larger tooth replacement part furthermore remains porous if sintering is too quick, whereby the edge of the tooth replacement part is fully sintered more rapidly.

The object of the present invention is therefore to provide a blank that permits higher heating rates in the heating phase without resulting in a fracture of the tooth replacement part, and without resulting in an undesirable esthetic impression of the tooth replacement part due to a porous core.

SUMMARY OF THE INVENTION

The invention relates to a blank for producing a tooth replacement part using a CAD/CAM device comprising a block of a sintered material. Said block of sintered material has already been presintered in a sintering furnace at an initial sintering temperature between 1000° C. and 1250° C.

The sintered material is a powder of ceramic particles with a zirconium dioxide (Y—$ZrO_2$) weight fraction of at least 90%, wherein a specific surface area of the powder is between 11 $m^2/g$ and 17 $m^2/g$.

The blank can comprise a blank holder and the block, for example, wherein, with respect to the dimensions of the block, the blank can correspond to the conventional blanks for known CAM processing machines. The tooth replacement part to be produced can, for example, be a complete denture for an implant, a dental prosthesis, a full crown, a partial crown, a bridge consisting of several whole teeth or an inlay. The CAD/CAM device includes a CAD unit, such as a computer, for planning and graphically displaying a 3D model of the tooth replacement part to be produced, and a CAM processing machine for carving out the tooth replacement part to be produced from a clamped blank according to the planned 3D model. The sintered material of the block can consist of a powder of ceramic particles, for example zirconium dioxide.

A polymer or a polymer mixture can be included as the binding agent. A two-phase binder system consisting of a polymer mixture, for example, can be used as the binding agent. The block of the sintered material has already been presintered. During presintering, the blank is presintered at the initial sintering temperature between 1000° C. and 1250° C. for a period of two hours, for example. The blank is slowly heated to the initial sintering temperature with a heating rate of no more than 5° C. per minute. The initial sintering temperature is then held for a holding time of no more than two hours, whereby the presintered blank is subsequently cooled. The heating rate of 5° C. per minute may not be exceeded, because this would result in mechanical stresses and fractures within the blank. After presintering, the blank is hard enough to be processed by means of the CAM processing machine. The sintering furnace can be a conventional sintering furnace, which is heated by thermal heating elements. The sintering furnace can also be an induction furnace, however, wherein a furnace chamber is heated by induction. The sintering furnace can also be a debinding furnace (bisque firing furnace).

The specific surface area of the powder, for example of ceramic particles, between 11 $m^2/g$ and 17 $m^2/g$ makes it possible for the tooth replacement part to be fully sintered more quickly, as a result of which the desired aesthetic impression of the tooth replacement part is achieved. The desired aesthetic impression is produced, because there are no residual pores in the core of the tooth replacement part that result in undesired diffused light in the interior of the tooth replacement part.

Zirconium dioxide is a classic sintered material and is particularly well-suited for the production of tooth replacement parts.

One advantage of this blank is that, due to the initial sintering temperature that is higher than that used for conventional blanks, a greater hardness and thermal conductivity of the presintered blank is achieved. In a heating phase when sintering the tooth replacement part to final density, a higher heating rate, such as 100° C. per minute, is consequently possible without fracturing the tooth replacement part. The initial sintering temperature cannot be too high, however. This is because excessive hardness of the presintered blank would result in increased wear on the tools of the CAM processing machine. The higher heating rate thus decreases the duration of the sintering of the tooth replacement part to final density.

The initial sintering temperature can advantageously be between 1050° C. and 1200° C.

An ideal hardness of the presintered blank is achieved with an initial sintering temperature between 1050° C. and 1200° C., for example 1150° C.

The block can advantageously be pressed with a pressing pressure between 130 and 250 MPa.

The blocks are pressed from the sintered material, consisting of ceramic particles and a polymer, by means of a press with a pressing pressure between 130 and 250 MPa. After presintering, the resulting density of the block can be 3.4 $g/cm^3$ at an initial sintering temperature of 1050° C. and 3.6 $g/cm^3$ at an initial sintering temperature of 1100° C.

The specific surface area of the powder can advantageously be between 12 $m^2/g$ and 14 $m^2/g$.

With such a specific surface area of the powder, particularly high heating rates are achieved during sintering to final density.

The sintered material of the block can advantageously include an yttrium oxide weight fraction between 2% and 4.5%.

Yttrium oxide is a ceramic precursor and is used as a classic stabilizer of zirconium dioxide. If the yttrium oxide weight fraction is too low, the tooth replacement part can fracture during the cooling phase.

The sintered material of the block can advantageously contain a dye, a combination of a number of dyes and/or at least one oxide or one chloride of a dye for coloring the block, wherein the dye is terbium, magnesium, cobalt, manganese and/or erbium.

In particular the dyes terbium for a yellow coloration and erbium for a red coloration are suitable as dyes for the block, because these dyes do not exhibit a change in valency during rapid cooling and therefore do not undergo a color change. The dye iron oxide for yellow coloration, on the other hand, exhibits a change in valency during too rapid cooling, so that the tooth replacement part acquires an undesirable green coloration as it cools. This results in undesirable colors for the tooth replacement part. The green coloration is due to the fact that oxygen cannot be reincorporated into the crystal lattice of the ceramic quickly enough. Oxides or chlorides of the abovementioned dyes can also be used as dyes.

The invention further relates to a method for producing a tooth replacement part from a blank comprising a block of a sintered material. Said block of sintered material is presintered in a sintering furnace at an initial sintering temperature between 1000° C. and 1250° C.

The abovementioned blank, for example, can be used for this method. The required hardness of the presintered blank for processing in the CAM processing machine is achieved with this initial sintering temperature.

One advantage of this method is that, due to the initial sintering temperature that is higher than that used for known presintered blanks, a greater hardness, and with it higher heating rates during the sintering of the produced tooth replacement part to final density, are made possible.

The block of the sintered material can advantageously be presintered at the initial sintering temperature between 1050° C. and 1200° C.

The desired hardness of the presintered blank is achieved at such an initial sintering temperature.

The block can advantageously be pressed by means of a pressing apparatus with a pressing pressure between 130 and 250 MPa.

The desired density of the pressed blank is achieved at such a pressing pressure of the pressing apparatus.

The tooth replacement part can advantageously be carved out of the presintered blank using a CAD/CAM device.

In doing so, the tools of the CAM processing machine of the CAD/CAM device are suitable for processing the presintered blank.

The carved out tooth replacement part can advantageously be sintered to final density in a sintering furnace according to a defined temperature profile.

The sintering furnace is controlled according to a defined temperature profile, so that a desired progression of the temperature within the furnace chamber is achieved. The temperature profile can be selected from a database of different temperature profiles, for example, or calculated individually as a function of the dimensions of the produced tooth replacement part, which are known from the planned 3D model of the tooth replacement part. The sintering to final density can include a first drying phase with a first heating rate, a heating phase with a second heating rate, a holding phase with a defined holding temperature for a defined holding time and a cooling phase with a defined cooling rate.

In a computer-aided method, a virtual largest possible sphere can be determined within the volume of the planned tooth replacement part by means of a search algorithm. The diameter of such a largest possible sphere in the volume of the planned tooth replacement part is then used as a geometric parameter for the selection or determination of a suitable temperature profile for the sintering to final density.

In the volume of the tooth replacement part, the tooth replacement part can advantageously comprise a largest possible sphere having a diameter under a limit value of 6 mm, wherein the temperature profile has a defined heating rate between 150° C./minute and 350° C./minute in a heating phase.

In the volume of the tooth replacement part, the tooth replacement part can advantageously comprise a largest possible sphere having a diameter under a limit value of 3 mm, wherein the defined heating rate is between 200° C./minute and 350° C./minute.

For a diameter of the largest possible sphere of less than 3 mm, the heating rate can be 250° C./minute, for example.

In the volume of the tooth replacement part, the tooth replacement part can advantageously comprise a largest possible sphere having a diameter above a limit value of 6 mm, wherein the temperature profile has a defined heating rate between 70° C./minute and 150° C./minute in a heating phase.

For a diameter of the largest possible sphere of more than 6 mm, the heating rate and a cooling rate, for example for zirconium dioxide, may not exceed 150° C./minute. This is because a higher heating rate could lead to thermal stresses during sintering and thus to cracks in the tooth replacement part. Undesirable pores, which would interfere with the desired esthetic translucency properties, could furthermore arise in the core of the tooth replacement part.

BRIEF DESCRIPTION OF THE DRAWINGS

The invention is explained with reference to the drawings. The drawings show.

DETAILED DESCRIPTION OF THE INVENTION

Figure 1:
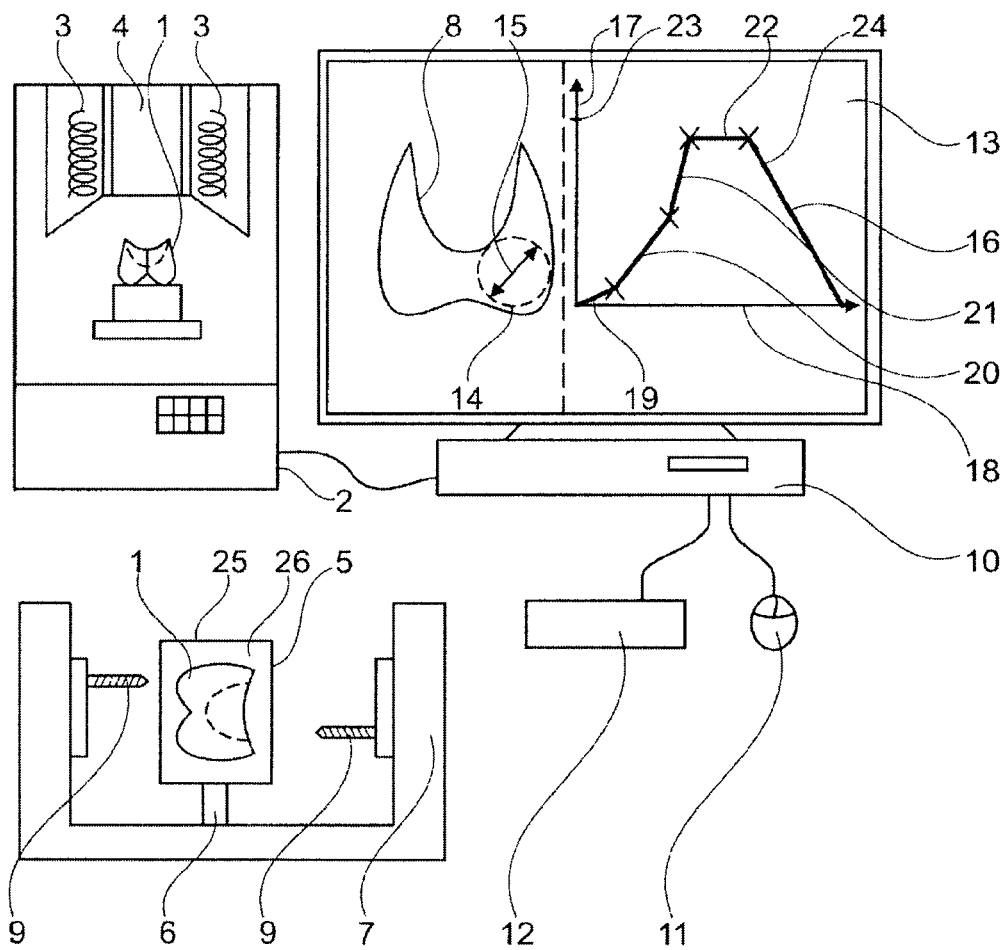
FIG. 1 a sketch to illustrate the present method for producing the tooth replacement part, FIG. 2 a temperature profile for presintering, FIG. 3 a temperature profile 40 for sintering the produced tooth replacement part to final density.

FIG. 1 shows a sketch for illustrating the present method for producing a tooth replacement part 1 by means of a sintering furnace 2. To regulate the furnace temperature within a furnace chamber 4, the sintering furnace comprises heating elements 3. An induction furnace which regulates the furnace temperature within the furnace chamber 4 can alternatively be used as well. In the first step, a blank 5 is presintered by means of a sintering furnace at an initial sintering temperature between 1000° C. and 1250° C. A large industrial furnace that can presinter multiple blanks at once is usually used as the sintering furnace. The presintered blank is subsequently clamped into a CAM processing machine 7 using a blank holder 6.

The tooth replacement part 1 to be produced is carved out by means of the CAM processing machine using processing tools 9 according to a planned 3D model 8 of the tooth replacement part 1. The planning of the 3D model is performed using a computer 10, to which operating elements such as a mouse 11 and a keyboard 12 are connected. The 3D model 8 is displayed by means of a display device 13, such as a monitor. A largest possible virtual sphere 14 within the volume of the 3D model 8 is sought using a computer method. A diameter 15 of the largest possible virtual sphere 14 is an essential measure for determining a temperature profile 16. To do this, the temperature 17 is plotted as a function of the time 18. The temperature profile 16 for sintering the produced tooth replacement part 1 to final density typically includes a drying phase 19 with a first heating rate, a first heating phase 20 with a second heating rate, a second heating phase 21 with a third heating rate, a holding phase 22 at a defined holding temperature 23 and a cooling phase 24 with a defined cooling rate. A suitable temperature profile 16 is selected from a database of different temperature profiles, for example, or determined individually as a function of the largest possible sphere 14. The heating rates and cooling rates for a tooth replacement part 1 having a diameter 15 of the largest possible sphere 14 above a limit value of 6 mm may not exceed a value of 150° C. per minute, for example. This is because this would lead to thermal stresses within the tooth replacement part 1 and thus to fractures. The blank 5 consists of a block 25 of a sintered material 26 and the blank holder 6.

Figure 2:
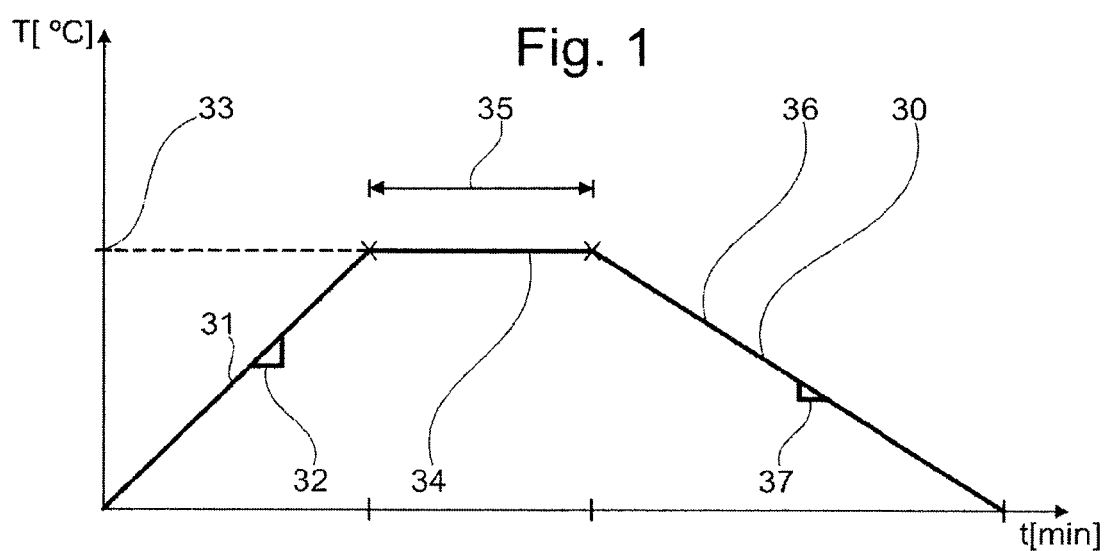

FIG. 2 shows a temperature profile 30 for presintering the blank 5 of FIG. 1. To do this, the temperature is plotted as a function of the time. In a heating phase 30 with a heating rate 32 of 50° C./hour, for example, the furnace temperature is heated to an initial sintering temperature 33 of, for example, 1100° C. In a holding phase 34, the initial sintering temperature 33 is subsequently held for a holding time 35 of, for example, 60 minutes. This is followed by a cooling phase 36 with a cooling rate 37 of, for example, 100° C./hour. The required hardness of the blank for processing in the CAM processing machine is achieved via the presintering. A too high initial sintering temperature 33 would lead to a hardness of the blank 5 that is so high that the tools 9 of the CAM processing machine of FIG. 1 would wear out more quickly.

Figure 3:
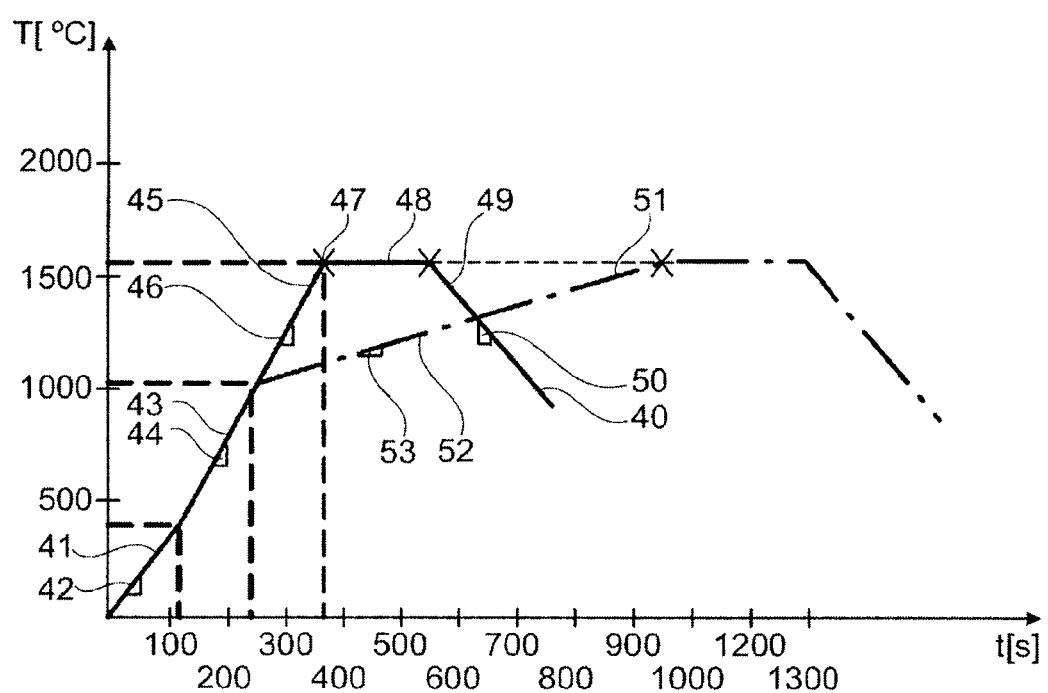

FIG. 3 shows a temperature profile 40 for sintering the produced tooth replacement part 1 to final density. In a drying phase 41, the furnace temperature is increased with a first heating rate 42 in 120 seconds to a temperature of 400° C. For a higher hardness of the produced tooth replacement part 1, the duration of the drying phase can also be decreased. In a first heating phase 43 with a second heating rate 44, the temperature is increased to a temperature of 1050° C. between 120 to 250 seconds. In a second heating phase 45 with a third heating rate 46 of 265° C. per minute, the furnace temperature is increased from a temperature of 1050° C. to a holding temperature 47 of 1580° C. in the time between 250 seconds and 370 seconds. In a holding phase 48, the holding temperature 47 is held for the time between 370 seconds and 550 seconds. The tooth replacement part 1 is then cooled in a cooling phase 49 with a cooling rate 50. The temperature profile 40 shown is for a presintered blank 5 with an initial sintering temperature 34 of 1100° C. The dash-dotted line shows a second temperature profile 51 for a tooth replacement part 1 from a presintered blank 5 that was presintered with an initial sintering temperature 34 of 960° C. The second heating phase 52 of the second temperature profile 51 has a significantly lower heating rate 53 of 45° C./minute. Due to the lesser hardness, a higher heating rate for a presintered blank with the initial sintering temperature of 960° C. would lead to mechanical stresses and fractures. The novel blank with the higher initial sintering temperature therefore makes a more rapid heating phase 45 possible, and thus decreases the duration of the sintering to final density.

The invention claimed is:

1. A blank for producing a tooth replacement part using a CAD/CAM device, the blank comprising;
a presintered block that has been heat-treated in a sintering furnace at an initial sintering temperature between 1000° C. and 1250° C. in order to obtain a predefined hardness and a mechanical structure of the block so that fracturing of the produced tooth replacement part at a defined heating rate corresponding to the initial sintering temperature, does not occur during sintering of the tooth replacement part, wherein the block is pressed from a powder of ceramic particles with a zirconium dioxide (Y—ZrO2) weight fraction of at least 90% and a specific surface area between 11 m2/g and 17 m2/g, such that a sintering time of the tooth replacement part is reduced, wherein the powder includes at least one dye and/or at least one oxide or chloride of a dye, for coloring the block, the at least one dye being terbium for a yellow color, which has no change in valence with rapid cooling and thus does not undergo a change in color.

2. The blank according to claim 1, wherein the initial sintering temperature is between 1050° C. and 1200° C.

3. The blank according to claim 1, wherein the block is pressed with a pressing pressure between 130 and 250 MPa.

4. The blank according to claim 1, wherein the specific surface area of the powder is between 12 and 14 m2/g.

5. The blank according to claim 1, wherein the powder includes an yttrium oxide weight fraction between 2% and 4.5%.

6. A method for producing a tooth replacement part from a blank according to claim 1, wherein the tooth replacement part is sintered to final density in a sintering furnace according to a defined temperature profile, wherein, in the volume of the tooth replacement part, the tooth replacement part includes a largest possible sphere having a diameter under a limit value of 6 mm, wherein the temperature profile has a defined heating rate between 150° C./minute and 350° C./minute in a heating phase and/or a defined cooling rate between 150° C./minute and 350° C./minute in a cooling phase.

7. The method according to claim 6, wherein, in the volume of the tooth replacement part, the tooth replacement part includes a largest possible sphere having a diameter under a limit value of 3 mm, wherein the defined heating rate is between 200° C./minute and 350° C. minute.

8. The blank according to claim 1, wherein the block is presintered ire order to obtain a predefined thermal conductivity of the block.

9. The blank according to claim 1, wherein the defined heating rate is between 150° C./minute and 350° C./minute.

10. The blank according to claim 1, wherein the defined heating rate is between 70° C./minute and 150° C. minute.

* * * * *